United States Patent
Overby et al.

(10) Patent No.: US 7,301,641 B1
(45) Date of Patent: Nov. 27, 2007

(54) FIBER OPTIC SMOKE DETECTOR

(75) Inventors: John K. Overby, Nottingham, PA (US); Stephen A. Mastro, Glen Mills, PA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 531 days.

(21) Appl. No.: 10/826,794

(22) Filed: Apr. 16, 2004

(51) Int. Cl.
*G01N 21/00* (2006.01)

(52) U.S. Cl. ............... 356/438; 250/343; 250/574; 356/436; 356/437

(58) Field of Classification Search ............... None
See application file for complete search history.

(56) References Cited

U.S. PATENT DOCUMENTS

| | | | | |
|---|---|---|---|---|
| 4,226,533 A | * | 10/1980 | Snowman | 356/338 |
| 4,230,950 A | * | 10/1980 | Forss et al. | 250/574 |
| 4,547,675 A | * | 10/1985 | Muggli et al. | 250/565 |
| 4,642,471 A | * | 2/1987 | Guttinger et al. | 250/574 |
| 5,352,901 A | * | 10/1994 | Poorman | 356/343 |
| 6,166,648 A | * | 12/2000 | Wiemeyer et al. | 356/438 |
| 6,565,352 B2 | * | 5/2003 | Nielsen et al. | 356/438 |

* cited by examiner

*Primary Examiner*—Gregory J. Toatley, Jr.
*Assistant Examiner*—Juan D Valentin, II
(74) *Attorney, Agent, or Firm*—Arthur K. Samora; Jacob Shuster

(57) ABSTRACT

A passive sensor housing has an air gap formed therein between a collimating lens and a lens focused mirror reflecting optical light signals transmitted through the lens into the air gap within which smoke is received through screened openings in the housing. The optical light signals which are generated within an opto-electronics unit are returned thereto by reflection through the air gap into a fiber cable connected to the collimating lens of the sensor and to an optical coupler within the opto-electronic unit to which generated light signals are delivered from a light emitting diode and returned from the sensor for delivery to a receiver within which such signals are processed into an output signal reflecting smoke density within the air gap.

3 Claims, 2 Drawing Sheets

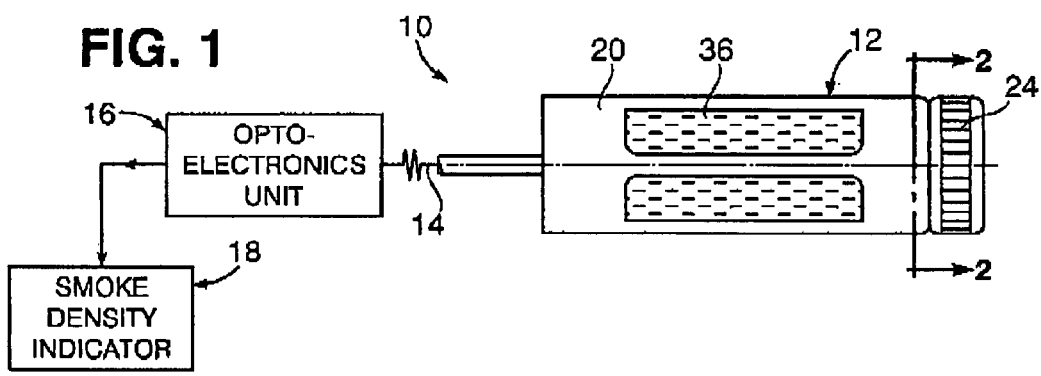
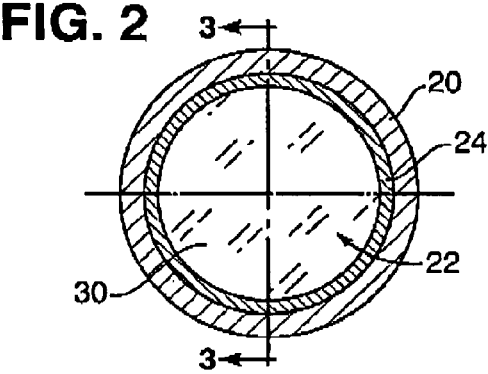
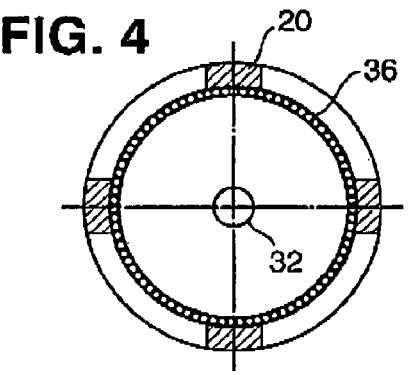
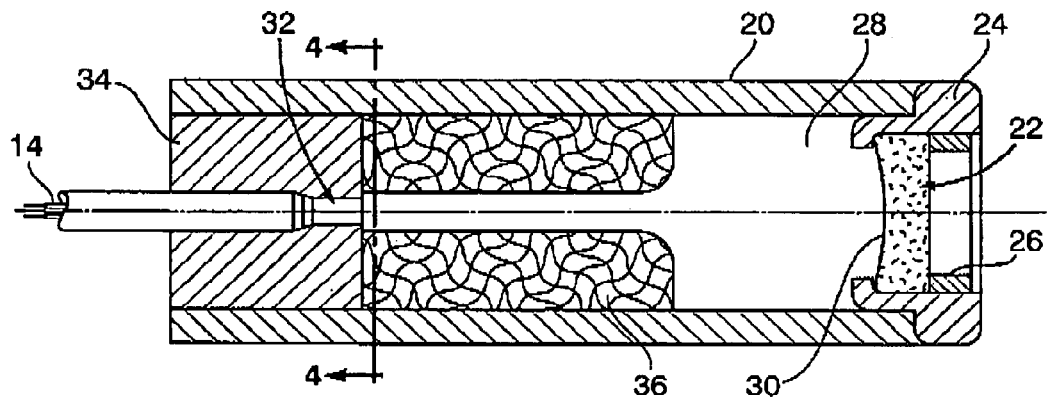

FIBER OPTIC SMOKE DETECTOR

The present invention relates generally to the detection of smoke.

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION

Smoke detection is presently concerned primarily with aerosol content of smoke produced by burning of material under different conditions which significantly affect aerosol property of the smoke, such as particle size and distribution quantified in terms of percentage obscuration involving the interaction of light wave radiation with the smoke aerosols producing scattering and absorption of the light waves due to the presence of the smoke. Currently there are two basic types of smoke detectors used for fire detection purpose when smoke density exceeds a certain threshold. One of such smoke detectors is of an ionization chamber type within which radioactive, charged plate electric field is established through which ionized air molecules migrate to trigger a fire indicating alarm. Such smoke detectors however have a high false alarm rate tendency caused by airborne dust and water droplets. False alarms caused by airborne dirt or water droplets are applicable to the other types of photoelectric smoke detectors, wherein smoke particles entering an optically powered illuminated test chamber scatter light in all directions causing light collection. It is therefore an important object of the present invention to provide a smoke detector which avoids the aforementioned false alarms and other disadvantages associated with the ionization chamber and aforementioned photoelectric types of smoke detectors.

SUMMARY OF THE INVENTION

Pursuant to the present invention, shifts in optical power spectrum of light returned from a passive sensor through a fiber cable is detected to measure smoke density. Light originating from an opto-electronic unit enters the sensor through the same fiber cable and is collimated through a lens before traversing a short length air gap for focused reflection by a mirror back through the lens and return through the fiber cable to the remotely located opto-electronic unit within which the light is generated and compared with the light being returned from the sensor to determine the optical spectrum shift and related obscuration within the sensor air gap.

BRIEF DESCRIPTION OF THE DRAWING

A more complete appreciation of the invention and many of its attendant advantages will be readily appreciated as the same becomes better understood by reference to the following detailed description when considered in connection with the accompanying drawing wherein:

FIG. 1 is a side elevation view of a smoke detector system in accordance with the present invention;

FIG. 2 is a transverse section view of the sensor shown in FIG. 1, taken substantially through a plane indicated by section line 2-2;

FIG. 3 is a longitudinal section view taken substantially through a plane indicated by section line 3-3 in FIG. 2;

FIG. 4 is a transverse section view taken substantially through a plane indicated by section line 4-4 in FIG. 3.

DETAILED DESCRIPTION OF THE PREFERRED EMBODIMENT

Figure 5:
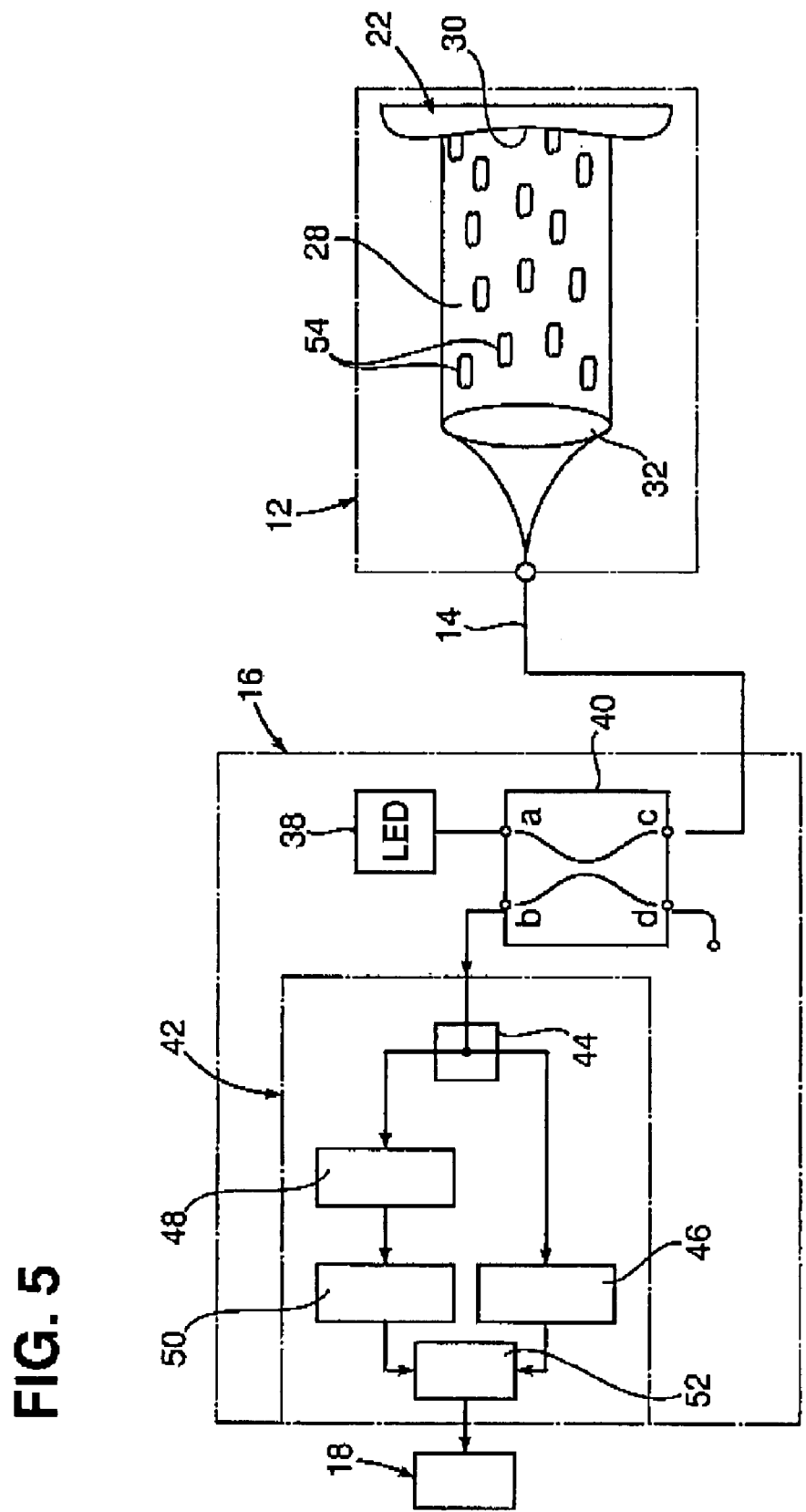
FIG. 5 is a schematic view and block diagram corresponding to the smoke detector system illustrated in FIG. 1.

Referring now to the drawing in detail, FIG. 1 illustrates a smoke detector system 10 featuring a sensor 12 adapted to be positioned within an air space test location for detection of smoke therein. The sensor 12 is connected by a fiber cable 14 to an opto-electronics unit 16 which may be remotely spaced therefrom. Standard smoke density data is transmitted from the unit 16 to an indicator 18, pursuant to the present invention as hereinafter explained.

As shown in FIGS. 1, 2, 3 and 4, the sensor 12 has an axially elongated cylindrical housing 20 closed at one axial end by a mirror 22 held in position within the housing 20 between a mirror mount 24 and a retention ring 26. An air gap 28 of relatively short axial length, such as 2 inches, is formed within the housing 20, sealed between a concave surface 30 of the mirror 22 focusing reflected optical signal light through the air gap 28 onto a graded-index micro-lens 32 positioned within a lens mount 34 closing the other axial end of the housing 20 opposite the mirror 22. Such lens 32 collimates the optical signal light entering into the lens mount 24 of the sensor 12 from the fiber cable 14 to prevent it from spreading outwardly across the air gap 28 within the housing 20. Also formed in the housing 20 as shown in FIGS. 1, 2 and 5 are angularly spaced openings in screening 36 through which inflow smoke may be received within the air gap 28.

Referring now to FIG. 5, the opto-electronics unit 16 is provided with a broad band light-emitting diode 38 centered around 465 manometers to produce an optical signal applied to one leg (a) of an optical coupler 40. One outgoing optical signal exits from the coupler 40 through its leg (c) to the sensor 12 through the fiber cable 14, from which a reflected optical signal is returned within the fiber cable 14 to the coupler leg (c) for reentry into the coupler 40. All optical signal light received within the coupler 40 through the legs (a) and (c) are exclusively routed through leg (b) to a receiver component 42 of the unit 16, while light routed to the leg (d) is ignored.

With continued reference to FIG. 5, the optical signals from the coupler 40 are fed to the receiver 42 for detection of varying effects of smoke by signal splitting through a divider 44 between one path directly to a detector 46 and a second path to a wavelength filter 48 before being fed to another detector 50. The filter 48 selectively passes only optical signals within the upper half of the optical spectrum of the LED diode as an originating optical signal source. The output signals from the detectors 46 and 50 are then passed into a processor 52 having coded hardware and software relating the varying signal values of the outputs of the detectors 46 and 50 to the amount of smoke obscuration by smoke particles 54 within the air gap 28 of the sensor 12 as shown in FIG. 5. Thus, as smoke enters the sensor air gap 28, the lower half of the optical signal spectrum will be absorbed more than the upper spectrum half due to the relationship of wavelength to smoke particle size, resulting in a greater percentage signal change in the output of the detector 46 than that of the output from the detector 50.

It will be apparent from the foregoing description that the smoke detector system 10 involves use of the sensor 12 which is completely passive in avoiding use of any operational power and may therefore be remotely located from the electronic unit 16 to which it is connected by the fiber cable 14 of any desired length. The sensor 12 is furthermore of a relatively short axial length, while use of the fiber cable 14 for signal transmission to and from the unit 16, as compared to use of copper wire signal lines, enables sensor operation under high temperature conditions. Also the sensor 12 because of its association with the unit 16 possesses the ability to suppress the adverse optical spectrum effect of ambient light noise from sources such as room lighting, flashlights, heat, etc. having flat and broad patterns.

Obviously, other modifications and variations of the present invention may be possible in light of the foregoing teachings. It is therefore to be understood that within the scope of the appended claims the invention may be practiced otherwise than as specifically described.

What is claimed is:

1. A smoke detector system comprising:
    a powered opto-electronics unit within which optical signals are generated for determination of smoke density;
    a passive sensor remotely located from the opto-electronics unit, said passive sensor including a housing having openings and enclosing an air gap exposed through said openings to smoke;
    a fiber optics cable interconnecting said opto-electronics unit and said passive sensor;
    collimating lens means mounted within the housing at one axial end thereof and connected to the fiber optics cable for transmission of said generated optical signals into the housing along an optical axis longitudinally centered in said passive sensor; and,
    focusing mirror means mounted within the housing at an opposite axial end of the housing for reflection of the optical signals along said optical axis, through the air gap and the lens means and into the fiber cable to be returned to the opto-electronics unit.

2. The system as defined in claim 1, wherein the opto-electronics unit further includes:
    light emitting diode means for generation of the optical signals within a predetermined optical spectrum;
    receiver means for detecting varying effects of the smoke on the optical signals returned through the fiber cable; and,
    optical coupler means connected to the receiver means.

3. The system as defined in claim 2, wherein the receiver means includes:
    signal divider means connected to optical coupler means for splitting transmission of the light signals received therefrom along two signal paths;
    filter means within one of said signal paths for passage of only the optical signals with an upper half of the optical spectrum;
    detector means for respectively detecting the optical signals transmitted from the filter means and along the other of said signal paths; and,
    signal processing means connected to said detector means for converting the optical signals received therefrom into an output signal reflecting obscuration of the air gap by the smoke received therein.

* * * * *